(12) United States Patent
Scrantz et al.

(10) Patent No.: US 8,828,061 B2
(45) Date of Patent: Sep. 9, 2014

(54) VERTEBRAL STABILIZATION DEVICES AND ASSOCIATED SURGICAL METHODS

(75) Inventors: Kelly Scrantz, Baton Rouge, LA (US); Fraser Landreneau, Baton Rouge, LA (US); Horace Mitchell, Baton Rouge, LA (US); Armando Varela, Boca Raton, FL (US); David Crook, Mineola, TX (US)

(73) Assignee: US Spine, Inc., Salt Lake City, UT (US)

( * ) Notice: Subject to any disclaimer, the term of this patent is extended or adjusted under 35 U.S.C. 154(b) by 502 days.

(21) Appl. No.: 12/051,202

(22) Filed: Mar. 19, 2008

(65) Prior Publication Data

US 2008/0234733 A1 Sep. 25, 2008

Related U.S. Application Data

(60) Provisional application No. 60/895,551, filed on Mar. 19, 2007.

(51) Int. Cl.
*A61B 17/70* (2006.01)
*A61B 17/02* (2006.01)

(52) U.S. Cl.
CPC ..... *A61B 17/7062* (2013.01); *A61B 2017/0256* (2013.01)
USPC ............ 606/276; 606/250; 606/251; 606/252

(58) Field of Classification Search
USPC ................................................ 606/246–279
See application file for complete search history.

(56) References Cited

U.S. PATENT DOCUMENTS

| 6,083,226 | A | * | 7/2000 | Fiz .................................. | 606/252 |
| 6,113,600 | A | * | 9/2000 | Drummond et al. .......... | 606/252 |
| 2002/0029039 | A1 | * | 3/2002 | Zucherman et al. ............ | 606/61 |
| 2002/0183749 | A1 | * | 12/2002 | Burgess et al. .................. | 606/61 |
| 2003/0153914 | A1 | * | 8/2003 | Oribe et al. ...................... | 606/61 |
| 2004/0092931 | A1 | * | 5/2004 | Taylor et al. .................... | 606/61 |
| 2004/0127906 | A1 | * | 7/2004 | Culbert et al. .................. | 606/72 |
| 2005/0240182 | A1 | * | 10/2005 | Zucherman et al. ............ | 606/61 |
| 2008/0109039 | A1 | * | 5/2008 | Michielli et al. ............... | 606/251 |

* cited by examiner

*Primary Examiner* — Jerry Cumberledge
*Assistant Examiner* — Nicholas Plionis
(74) *Attorney, Agent, or Firm* — Phillips Ryther & Winchester; Matthew D. Thayne

(57) ABSTRACT

A vertebral stabilization device operable for stabilizing and/or decompressing a portion of the spine, including: a first frame member; a second frame member; a first connector member engaged to the first frame member for securing the first frame member to a first structure of the spine; and a second connector member engaged to the second frame member for securing the second frame member to a second structure of the spine; wherein the first frame member and the second frame member are in a telescoping relationship with each other. The first and second structures of the spine may include spinous processes, laminae, sacral structures, or any other suitable structures. Preferably, the first connector member and the second connector member are substantially arcuate in shape, and may face towards each other, away from each other, or in the same direction.

12 Claims, 19 Drawing Sheets

VERTEBRAL STABILIZATION DEVICES AND ASSOCIATED SURGICAL METHODS

CROSS-REFERENCE TO RELATED APPLICATION

The present non-provisional patent application claims the benefit of priority of U.S. Provisional Patent Application No. 60/895,551, filed on Mar. 19, 2007, and entitled "VERTEBRAE STABILIZATION DEVICE," the contents of which are incorporated in full by reference herein.

FIELD OF THE INVENTION

The present invention relates generally to surgically implanted medical devices. More specifically, the present invention relates to vertebral stabilization devices that are surgically implanted adjacent to and selectively engaged with a portion of the spine of a patient at multiple levels in order to decompress and/or stabilize that portion of the spine, either statically or dynamically, in the treatment of an injury, a disease, and/or a degenerative condition. These vertebral stabilization devices may be surgically implanted via open or, preferably, minimally-invasive procedures.

BACKGROUND OF THE INVENTION

Lumbar spinal stenosis, for example, is characterized by a tightening of or decrease in the cross-sectional diameter of the spinal canal and neural foramen, through which the spinal cord and nerve roots of the lumbar (lower) spine pass, caused by the degeneration of the lumbar discs (through fluid loss and collapse) and the facet joints of the spinal column. In lumbar spinal stenosis, the lumbar discs deteriorate and the lumbar disc spaces collapse, resulting in a portion of the lumbar discs protruding into the ventral or anterior (front) portion of the spinal canal. At the same time, the two facet joints associated with each lumbar vertebrae become arthritic, growing in size, and protruding into the dorsal or posterior (back) portion of the spinal canal. Thus, the cross-sectional diameter of the spinal canal is decreased, impinging on the spinal cord and nerve roots of the lumbar spine. In addition, the ligamentum flavum that connect the bases of the spinous processes of the spinal column and the lamina tend to buckle with lumbar disc collapse, further decreasing the cross-sectional diameter of the spinal canal. The neural foramen, through which the nerve roots exit, are pinched with disc collapse and facet joint arthropathy. This condition is especially common in the elderly and symptoms may include remitting or unremitting pain and/or weakness/numbness in the middle to lower back and/or legs when moving and/or stationary. It should be noted that similar problems can occur in the cervical (upper) spine as well.

Conventional treatments for lumbar spinal stenosis include oral and/or injectable analgesic and/or anti-inflammatory medications (non-steroidal and/or steroidal), activity avoidance and/or physical therapy, braces, and/or surgical procedures. Surgical procedures for lumbar spinal stenosis include laminectomies/laminotomies and/or spinal fusions. In a laminectomy/laminotomy, all or a portion of a given facet joint, lamina, and ligamentum flavum are removed to alleviate compression of the spinal canal. This procedure basically "unroofs" or enlarges a portion of the spinal canal. Additionally, a spinal fusion may be performed. In a spinal fusion, a connecting bar and a bone graft are used to join or fuse adjacent vertebrae via a plurality of pedicle screws, thus stabilizing the vertebral segment. Much, if not all, of a given lumbar disc is removed in conjunction with a spinal fusion. In general, a spinal fusion is most suitable when there is instability or translation between adjacent vertebrae (spondylolisthesis). Disadvantageously, the plurality of pedicle screws used to perform a spinal fusion may become loose with the passage of time if a nonunion develops. Both laminectomies/laminotomies and spinal fusions are major, open procedures, typically requiring a relatively large incision and a general anesthetic. This may be dangerous for the elderly or the sick. In addition, both procedures are very expensive.

What has been observed clinically is that many patients, when they flex forward, experience an increase in the cross-sectional diameter of the spinal canal and neural foramen, thus alleviating or eliminating their pain and/or weakness/numbness caused by lumbar spinal stenosis. This is caused by the temporary distraction of the spinous processes and the "stretching out" of the ligamentum flavum that connect the bases of the spinous processes and lamina. The collapsed neural foramen are also increased in height and cross-sectional area by the distraction. In other words, the lumbar discs and other structures of the spinal column are temporarily decompressed. This observation has led to improved treatments for lumbar spinal stenosis, for example.

In this lumbar spinal stenosis example, it is desirable to develop devices and surgical methods for distracting adjacent spinous processes, or the laminae at the bases of the adjacent spinous processes, apart. It may also simply be desirable to stabilize these adjacent spinous processes, or the laminae at the bases of these adjacent spinous processes, in the treatment of other conditions. It may further be desirable to distract and/or stabilize a spinous process, or the laminae at the base of the spinous process, with respect to the sacrum of the spine. In each case, both static and dynamic devices and surgical methods are desirable. Thus, what are needed in the art are such vertebral stabilization devices and associated surgical methods.

BRIEF SUMMARY OF THE INVENTION

In one exemplary embodiment, the present invention provides a vertebral stabilization device operable for stabilizing and/or decompressing a portion of the spine, including: a first frame member; a second frame member; a first connector member engaged to the first frame member for securing the first frame member to a first structure of the spine; and a second connector member engaged to the second frame member for securing the second frame member to a second structure of the spine; wherein the first frame member and the second frame member are in a telescoping relationship with each other. The first and second structures of the spine may include spinous processes, laminae, sacral structures, or any other suitable structures. Preferably, the first connector member and the second connector member are substantially arcuate in shape, and may face towards each other, away from each other, or in the same direction. Preferably, the first frame member is received partially into the second frame member for forming the telescoping relationship. The vertebral stabilization device also includes a securement mechanism positioned on the second frame member for providing a secured arrangement between the first frame member and the second frame member. The vertebral stabilization device further includes mutually overlapping receiving bores defined by the first frame member and the second frame member for receiving a screw. The connector members also include a bore defined by the first connector member for receiving a bone screw and a bore defined by the second connector member for receiving a bone screw.

In another exemplary embodiment, the present invention provides a vertebral stabilization device operable for stabilizing and/or decompressing a portion of the spine, includes: a first frame member; a second frame member comprising a recess defined by the body of the second frame member for partially receiving the first frame member, forming a telescoping relationship between the first frame member and the second frame member; a first connector member engaged to the first frame member for securing the first frame member to a first structure of the spine; a second connector member engaged to the second frame member for securing the second frame member to a second structure of the spine; and a securement mechanism for securing the first frame member to the second frame member and preventing telescoping movement of the first frame member with respect to the second frame member. The vertebral stabilization device also includes a set screw positioned on the second frame member for preventing telescoping movement between the first frame member and the second frame member. The vertebral stabilization device further includes a rack and pinion mechanism for adjusting telescopically the first frame member with respect to the second frame member. The vertebral stabilization device still further includes a rack positioned on the first frame member and a pawl positioned on the second frame member, wherein the pawl engages the rack, thus preventing telescoping movement of the first frame member with respect to the second frame member. The vertebral stabilization device still further includes a locking collet. The vertebral stabilization device still further includes integral pads associated with each of the first frame member and second frame member for the attachment of a decompression/distraction instrument to the vertebral stabilization device. Optionally, the first frame member includes a ball pivot positioned on its distal end and the second frame member includes a ball pivot positioned on its distal end. Optionally, each frame member includes a ball joint housing including a recess defined thereby for receiving the ball pivot.

In a further exemplary embodiment, the present invention provides a vertebral stabilization device operable for stabilizing and/or decompressing a portion of the spine, including: a first frame member; a second frame member including a recess defined by the body of the second frame member for partially receiving the first frame member, forming a telescoping relationship between the first frame member and the second frame member; a first substantially arcuate connector member having a top portion and a bottom portion, wherein the top portion includes a bore for receiving a bone screw, and the bottom portion includes a sheath for receiving a tip of the bone screw; a second substantially arcuate connector member having a top portion and a bottom portion, wherein the top portion includes a bore for receiving a bone screw, and the bottom portion includes a sheath for receiving a tip of the bone screw; and a securement mechanism for securing the first frame member to the second frame member and preventing telescoping movement of the first frame member with respect to the second frame member. The vertebral stabilization device also includes a rack positioned on the first frame member. The vertebral stabilization device further includes a locking collet including a screw casing and an internal bore, wherein a set screw is positioned within the screw casing and a mating rack is positioned within the internal bore. The vertebral stabilization device still further includes a distal washer positioned on the bottom portion of the first substantially arcuate connector member and a distal washer positioned on the bottom portion of the second substantially arcuate member. The vertebral stabilization device still further includes a snap ring for engaging the distal washer to the bottom portion of the first substantially arcuate connector member and a snap ring for engaging the distal washer to the bottom portion of the second substantially arcuate connector member. The vertebral stabilization device still further includes a slot positioned on the second frame member for receiving a pin positioned on the first frame member.

BRIEF DESCRIPTION OF THE DRAWINGS

The present invention is illustrated and described herein with reference to the various drawings, in which like reference numbers are used to denote like device components/surgical method steps, as appropriate, and in which.

DETAILED DESCRIPTION OF THE INVENTION

Figure 1:
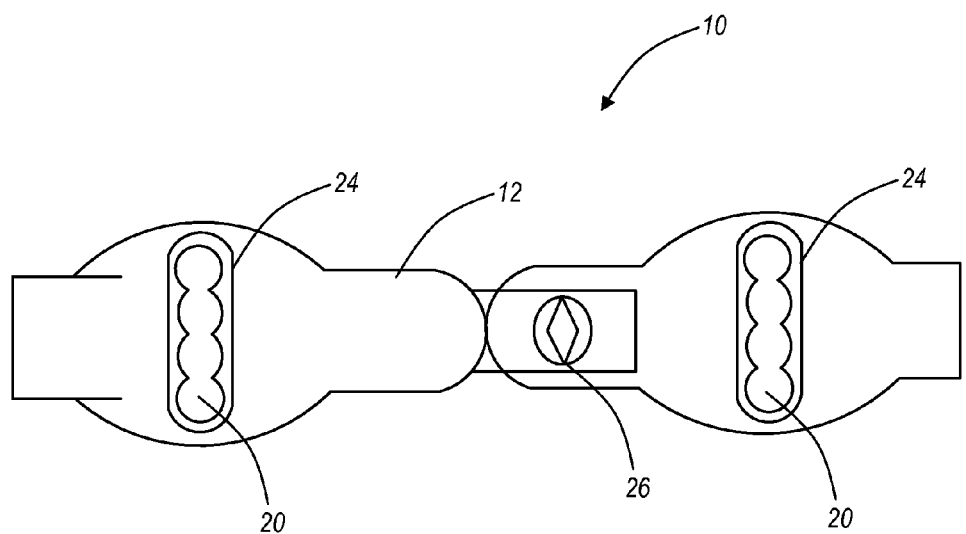
FIG. 1 is a top view of one exemplary embodiment of a vertebral stabilization device of the present invention.

Referring now specifically to the various drawings, an exemplary vertebral stabilization device is illustrated in FIG. 1 and is shown generally at reference number 10. As illustrated, the vertebral stabilization device 10 has a first frame member 12 and a second frame member 14. The first frame member 12 and the second frame member 14 are in a telescopic relationship with each other. Specifically, the first frame member 12 is partially received within the body of the second frame member 14 for attaching the first frame member 12 to the second frame member 14 and allowing the first frame member 12 and second frame member 14 to collectively expand and contract as a unified whole.

Figure 2:
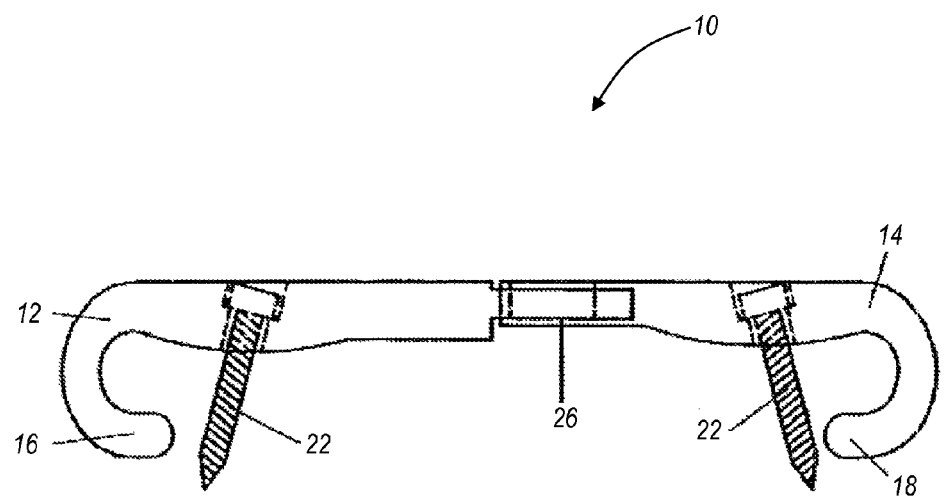
FIG. 2 is side view of the vertebral stabilization device of FIG. 1.
Figure 3:
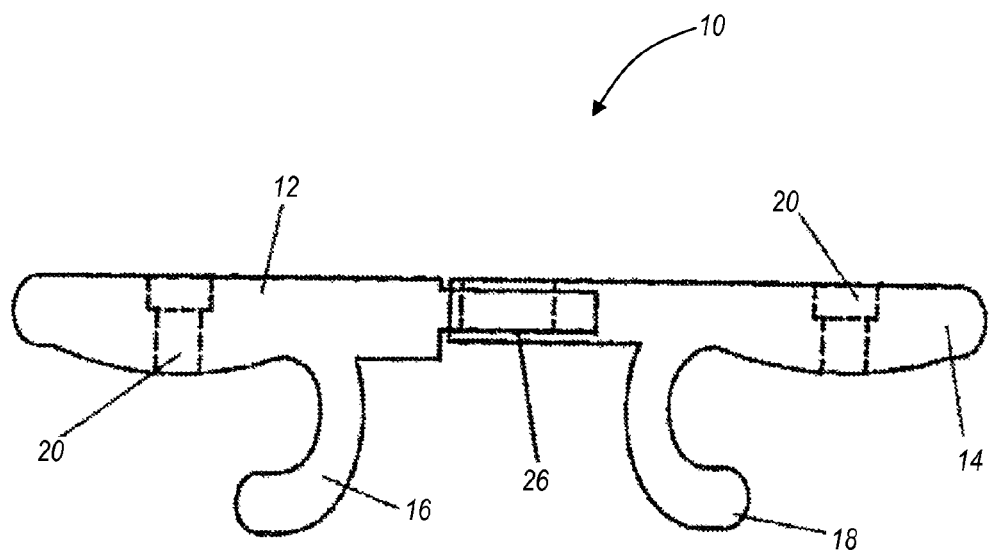
FIG. 3 is a side view of another exemplary embodiment of a vertebral stabilization device of the present invention.

A first connector member 16 is coupled to or integrally formed with the first frame member 12 and a second connector member 18 is coupled to or integrally formed with the second frame member 14, as illustrated in FIG. 2. The connector members 16, 18 are preferably arcuate in shape for fittingly connecting the vertebral stabilization device 10 to adjacent spinous processes, for example. In one exemplary embodiment, the connector members 16, 18 face arcuately towards each other, as illustrated in FIG. 2. In another exemplary embodiment, the connector members 16, 18 face acutely opposite each other, as illustrated in FIG. 3. Thus, the connector members 16, 18 are configured to fittingly engage either the proximal or distal surfaces of the adjacent spinous processes, for example. Each connector member 16, 18 contains mutually overlapping receiving bores 20 (FIGS. 1 and 3) for receiving a bone screw 22 (FIG. 2). The bores 20 further include a seat 24 (FIG. 1) for engaging the head of the bone screw 22. As illustrated in FIG. 1, the bores 20 may each include multiple positions for receiving the bone screw 22 (e.g. four positions are illustrated). The bores 20 define positions for the placement of the screws 22 at multiple locations.

A securement mechanism 26 is positioned on/through the second frame member 14 for selectively and securely engaging the first frame member 12 to the second frame member 14. As described above, the first frame member 12 is partially received within the body of the second frame member 14, forming a selectively secured telescopic relationship between the frame members 12, 14. The securement mechanism 26 exerts a stabilizing force on the first frame member 14. For example, the securement mechanism 26 is rotated, causing the securement mechanism 26 to move in a downward direction, until it is engaged to the first frame member 12, thus preventing further movement of the first frame member 12 relative to the second frame member 14.

The vertebral stabilization device 10 may have any shape and size to perform the intended function and realize the scope of the present invention. For example, the height of the vertebral stabilization device 10 may range from about 0.5 inches to about 0.75 inches, and the length of the vertebral stabilization device 10 may range from about 2.5 inches to about 2.75 inches, although other suitable dimensions are contemplated, depending upon the specific application.

Figure 4:
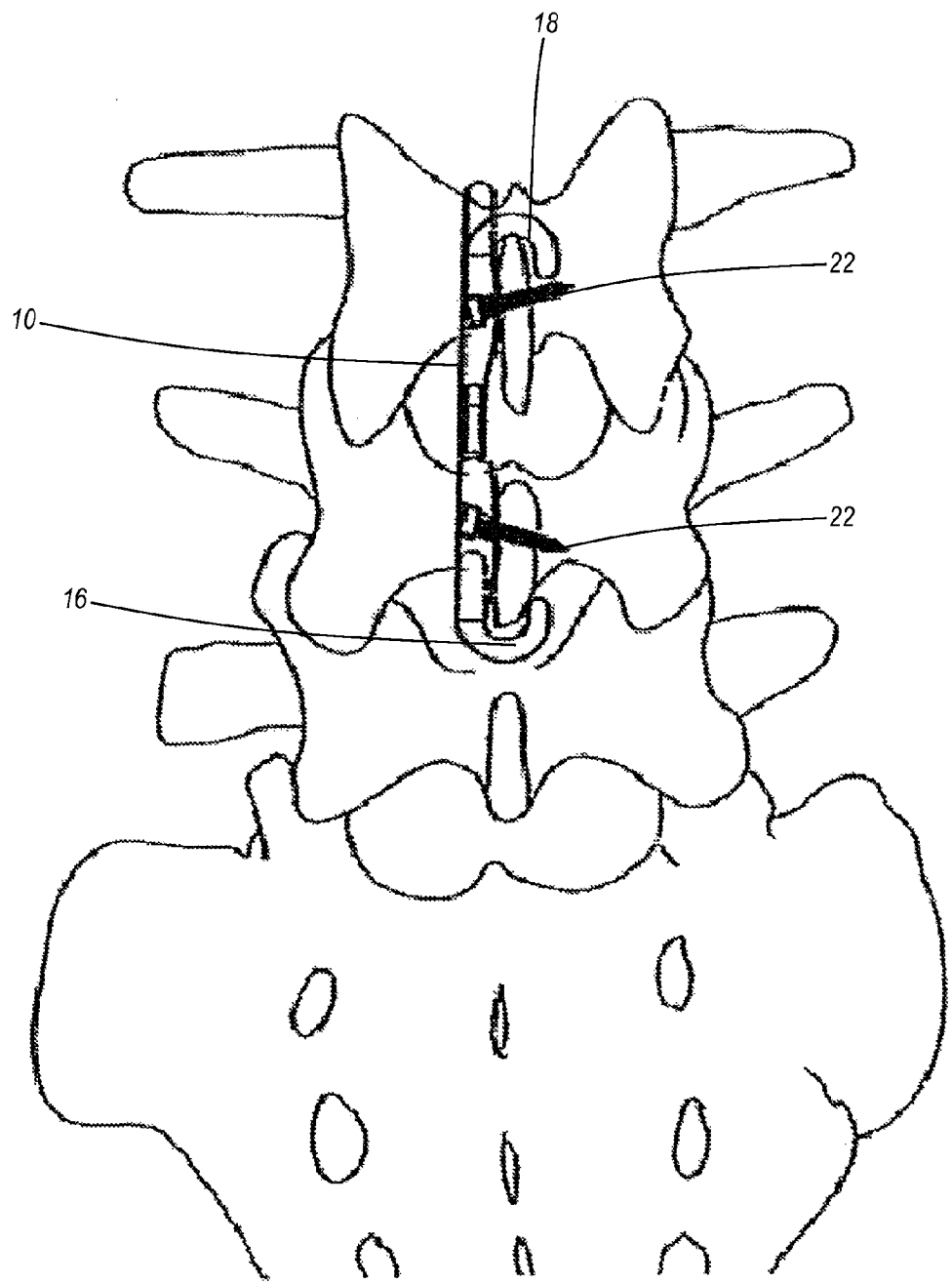
FIG. 4 is a side view of the vertebral stabilization device of FIGS. 1 and 2 attached to adjacent spinous processes of a spine, the vertebral stabilization device of FIG. 3 being surgically implanted in a similar manner.

FIG. 4 illustrates the vertebral stabilization device 10 in use. The connector members 16, 18 selectively secure the vertebral stabilization device 10 to adjacent spinous processes, while the bone screws 22 are selectively screwed into the bodies of the adjacent spinous processes. Due to its telescoping nature and the presence of the securement mechanism 26 (FIGS. 1-3), the vertebral stabilization device 10 may be used to stabilize the adjacent spinous processes and, if desired, compress them together, especially in the embodiment of FIGS. 1 and 2, or distract them apart, especially in the embodiment of FIG. 3. Alternatively, the vertebral stabilization device 10 may be coupled to other spinal structures, including, but not limited to, adjacent laminae, a spinous process and a lamina, a spinous process and the sacrum, a lamina and the sacrum, etc. All that needs to be varied in such applications are the relative angles of the connector members 16, 18 with respect to the rest of the vertebral stabilization device 10. In other words, the same vertebral stabilization device 10 must simply be configured with respect to size and angles such that the desired structures are fittingly engaged and the bone screws 22 have a substrate with which to mate.

Figure 5:
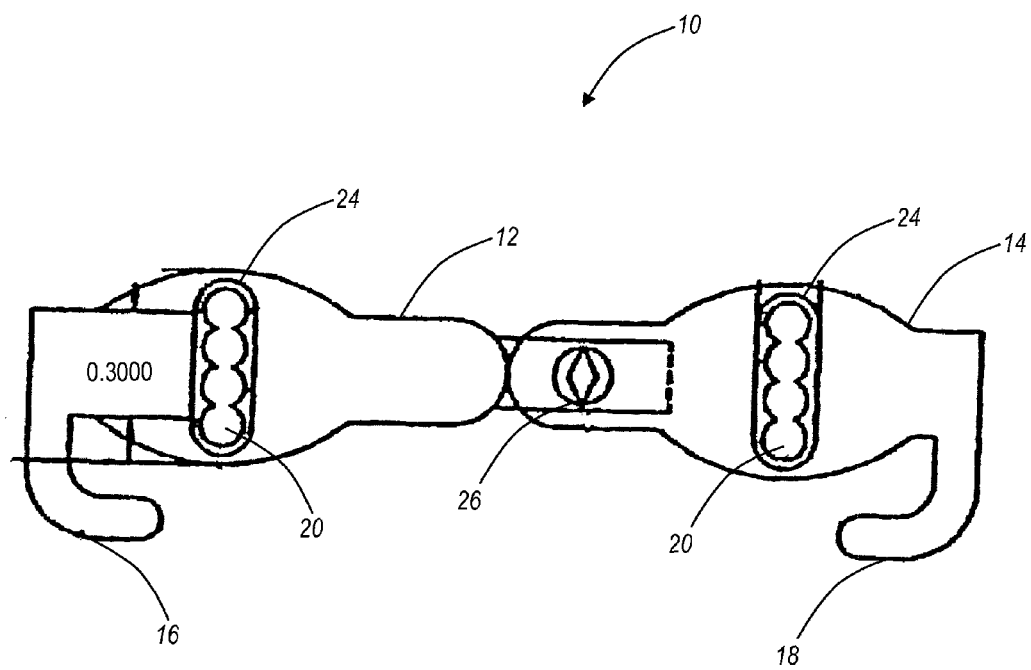
FIG. 5 is a top view of a further exemplary embodiment of a vertebral stabilization device of the present invention.
Figure 6:
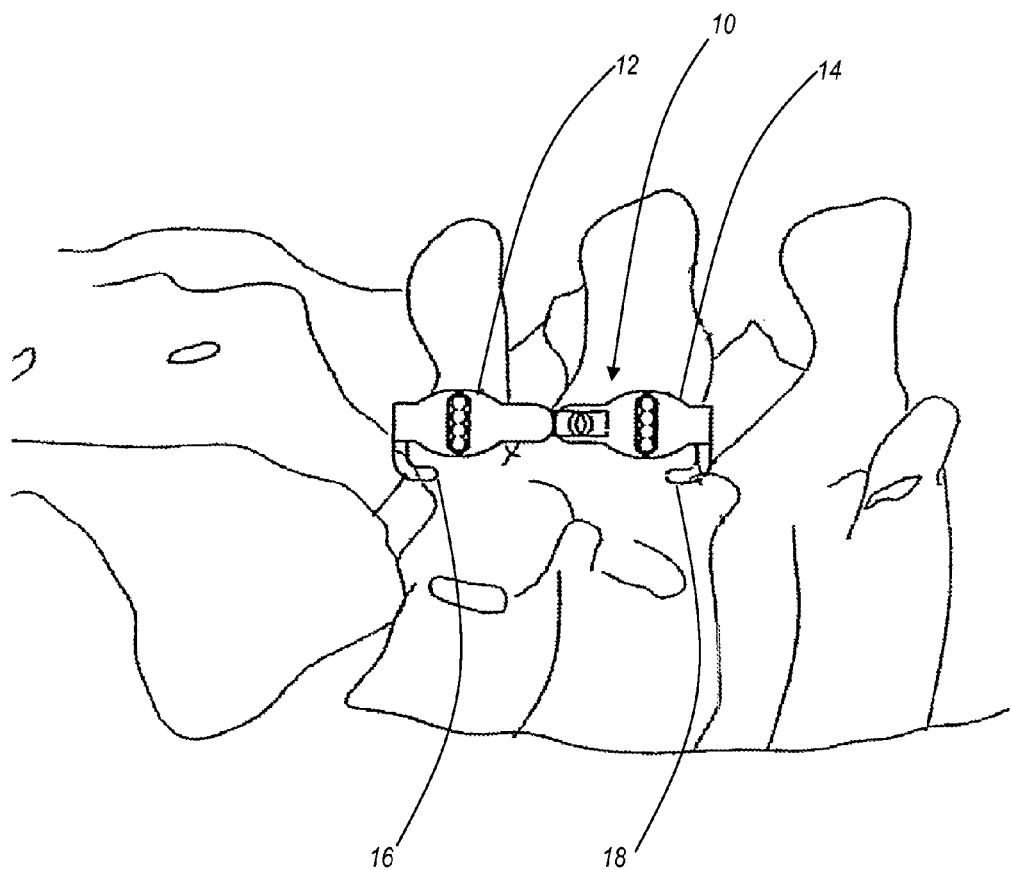
FIG. 6 is a top view of the vertebral stabilization device of FIG. 5 attached to adjacent laminae of a spine.

FIG. 5 illustrates a vertebral stabilization device 10 that is configured to engage such adjacent laminae, at the base of adjacent spinous processes, and FIG. 6 illustrates this vertebral stabilization device 10 actually engaging such adjacent laminae. Again, the relative angles of the connector members 16, 18 are simply varied with respect to the rest of the vertebral stabilization device 10, the vertebral stabilization device 10 becoming generally more "flat," in that the connector members 16, 18 protrude less from the "bottom" and more to the "side" of the vertebral stabilization device 10, such that the morphology of the adjacent laminae is more accurately addressed.

Figure 7:
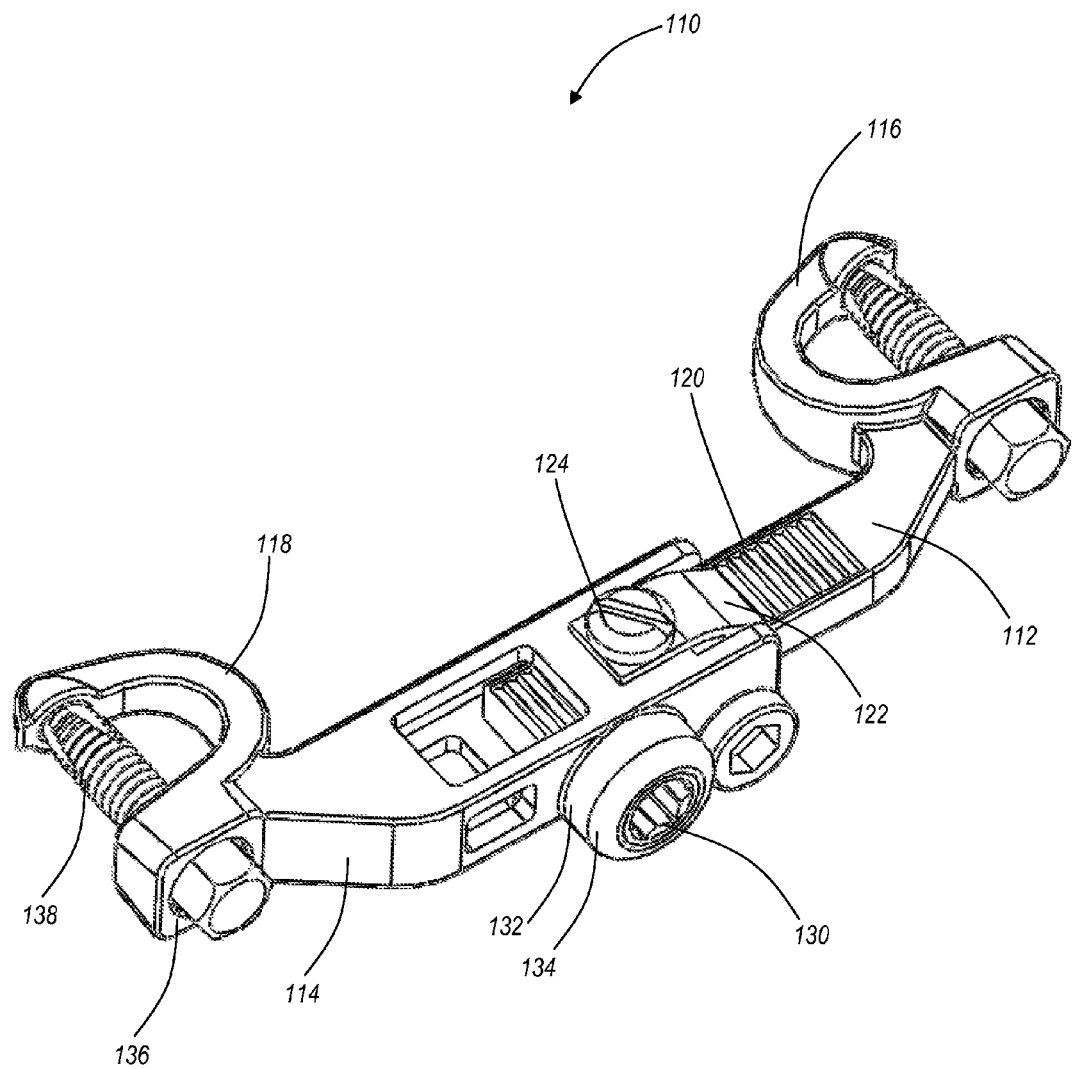
FIG. 7 is a perspective view of a still further exemplary embodiment of a vertebral stabilization device of the present invention.
Figure 8:
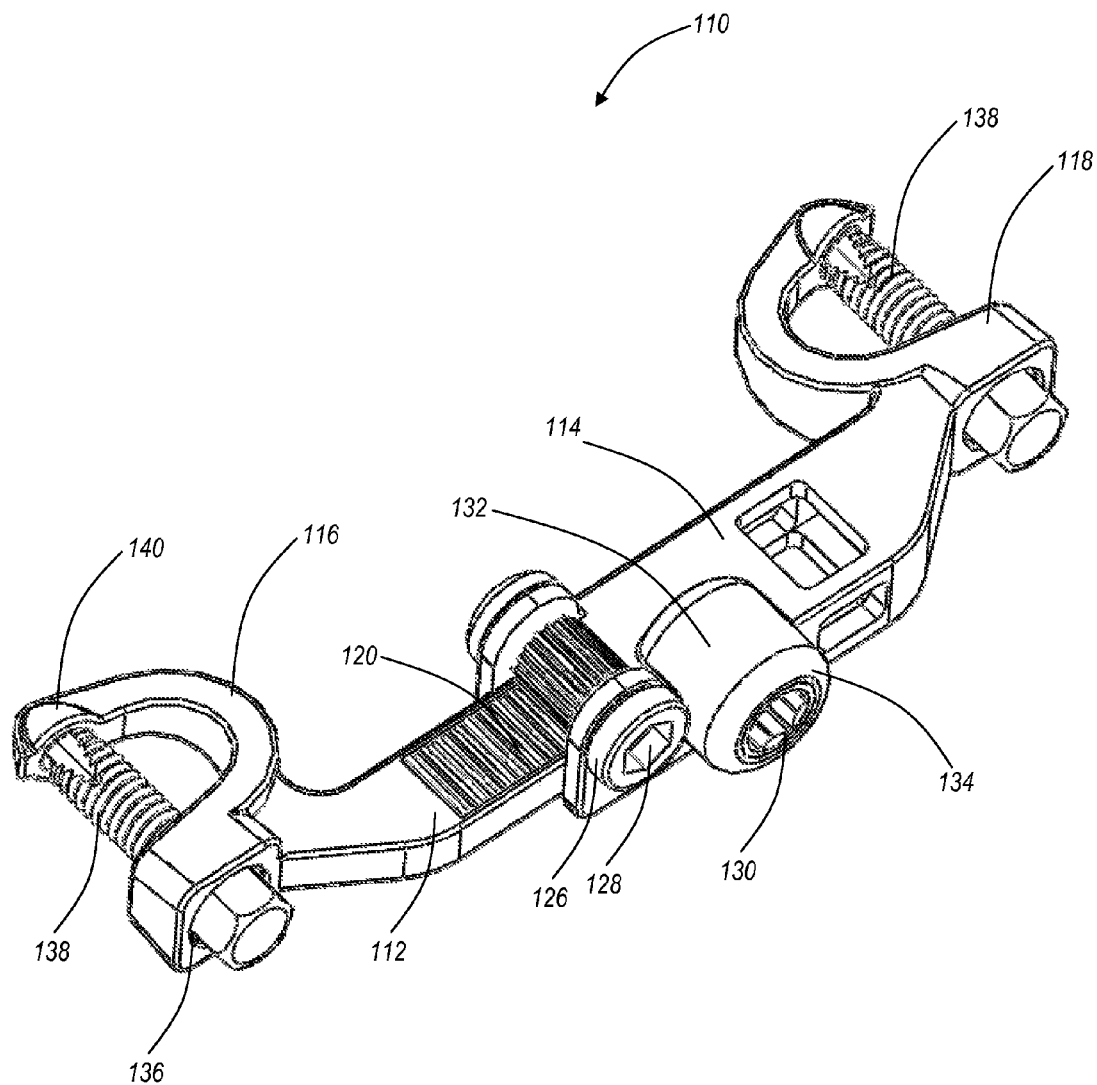
FIG. 8 is another perspective view of the vertebral stabilization device of FIG. 7.

FIGS. 7 and 8 represent another exemplary embodiment of the vertebral stabilization device 110 of the present invention. As illustrated, the vertebral stabilization device 110 has a first frame member 112 and a second frame member 114. The first frame member 112 and second frame member 114 are in a telescopic relationship with each other, such that proper fit with and, optionally, spinal structure distraction is possible. Specifically, the first frame member 112 is received partially within the body of the second frame member 114 for selectively attaching the first frame member 112 to the second frame member 114 and allowing the first frame member 112 and second frame member 114 to collectively expand and contract as a unified whole.

The exemplary embodiment contemplates a number of ways to secure the first frame member 112 to the second frame member 114. As illustrated in FIG. 7, a rack 120 is formed within the body of the first frame member 112. A pawl 122 is positioned on the second frame member 114 and engaged to the second frame member 114 by a screw 124 or the like. The pawl 122 is designed to be inserted between the ridges of the rack 120, and the screw 124 is selectively tightened to the second frame member 114, forming a secure arrangement between the first frame member 112 and the second frame member 114. The pawl 122 prevents the first frame member 112 from moving when secured, but also allows the appliance 110 to be adjustable when the pawl 122 is unsecured.

The first frame member 114 may be adjusted with respect to the second frame member 112 by way of a pinion 126 in an engaged relationship with the rack 120. The pinion 126 is disposed on the side opposite the pawl 122, allowing the frames 112, 114 to be adjusted and then secured in a stationary relationship by the pawl 122. In other words, the pawl 122 is an anti-slip feature that allows the secure locking post distraction or decompression.

The pinion 126 contains a recess 128 designed to receive a tool for selectively rotating or turning the pinion 126. In the exemplary embodiment of FIG. 8, the recess is designed to receive a hexagonal driver (not illustrated). As the pinion 126 is selectively rotated or turned, the ridges of the pinion 126 intersect the ridges of the rack 120, forcing the rack 120 to translate. The rack 120 and pinion 126 are designed for self-distraction/compression in-situ without instrumentation.

A set screw 130 is disposed on the top of the vertebral stabilization device 110 for securing the second frame member 114 within the first frame member 112. The set screw 130 is positioned within a casing 132 that forms a lip 134 on the first frame member 112. The screw 124 is positioned within the casing 132 and is flush or slightly lower than the lip 134 for receiving a tool to rotate the screw 124. When the screw 124 is rotated, the screw 124 exerts a force upon the second frame member 114, securing the first frame member 114 within the second frame member 112. Optionally, the vertebral stabilization device 110 is designed to allow a single instrument to rotate the screw 124, pinion 126, and set screw 130 of the vertebral stabilization device 110 in-situ.

Each frame member 112, 114 includes a first connector member 116 and a second connector member 118, respectively, as illustrated in FIGS. 7 and 8. The connector members 116, 118 are substantially arcuate in shape. The top portion of the connector members 116, 118 contain a bore 136 for receiving a bone screw 138 therethrough. Optionally, the top portion of the connector members 116, 118 contain a threaded bore 136 for receiving a correspondingly threaded bone screw 138 therethrough. The bottom portion of the connector members 116, 118 contain a sheath 140 for receiving the tip of the bone screw 138. The sheath 140 has a diameter slightly larger than the diameter of the head of the bone screw 138 for securely receiving the bone screw 138 within the sheath 140. The sheath 140 protects the tissues from the sharp tip of the bone screw 138. Optionally, the bore 136 may contain a seat (not illustrated) within the bore 136 for positioning the head of the bone screw 138. Optionally, the first frame member 112 and second frame member 114 have a wedge shaped leading edge, nearest the respective connection member 116, 118, that supports a less invasive, lateral surgical approach.

Figure 9:
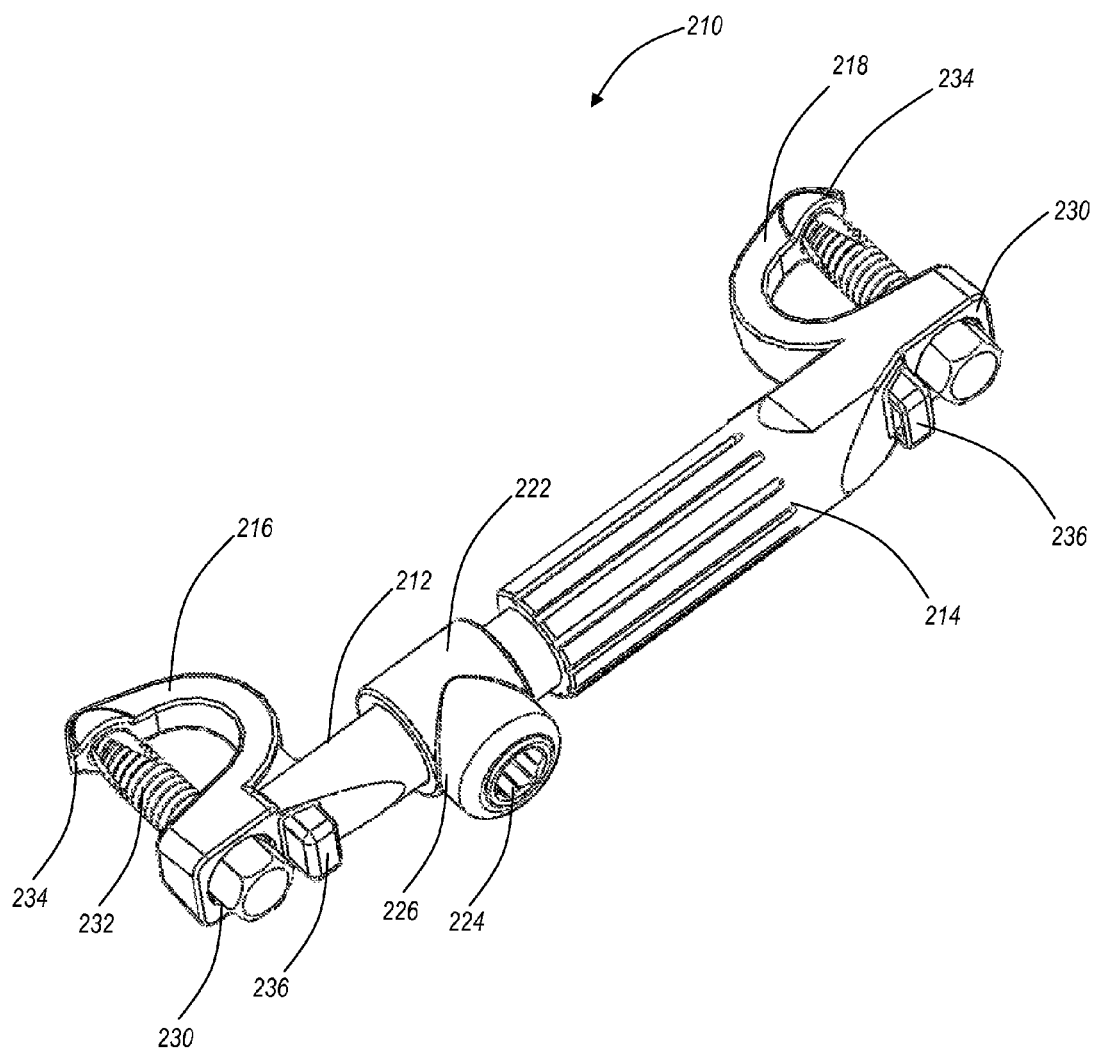
FIG. 9 is a perspective view of a still further exemplary embodiment of a vertebral stabilization device of the present invention.
Figure 10:
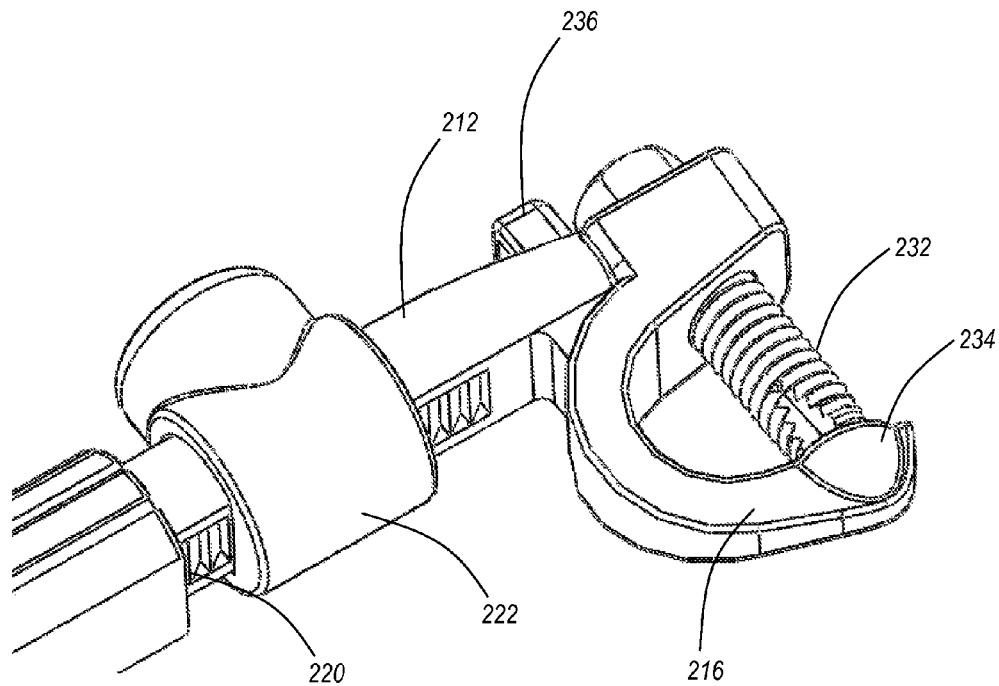
FIG. 10 is a partial perspective view of the vertebral stabilization device of FIG. 9.
Figure 11:
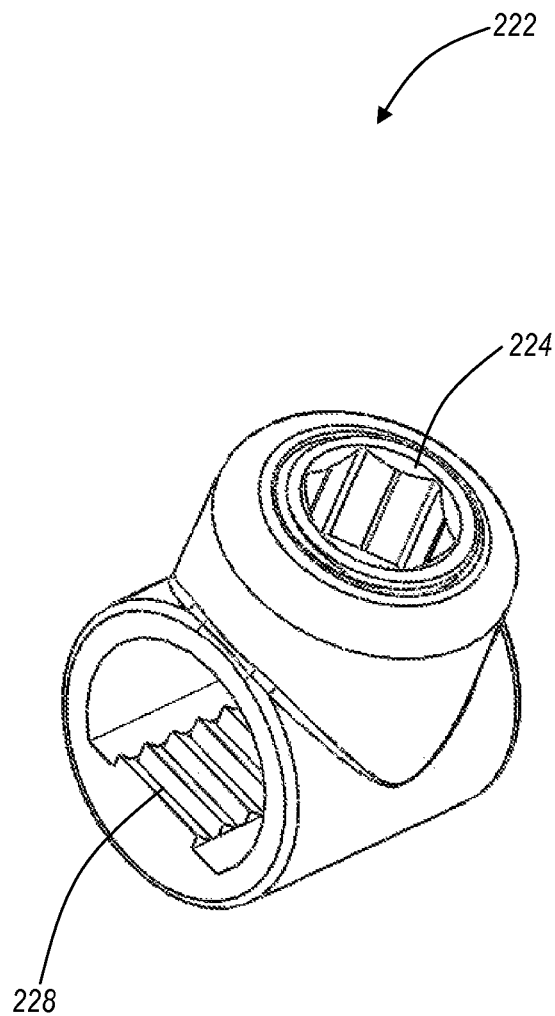
FIG. 11 is a perspective view of the locking collet of the vertebral stabilization device of FIGS. 9 and 10.

Another exemplary embodiment of the vertebral stabilization device 210 is illustrated in FIG. 9. In this embodiment, the first frame member 212 is received into the second frame member 214 to form a telescoping relationship. The first frame member 212 includes a rack 220, as illustrated in FIG. 10, with a plurality of ridges disposed on one side of the first frame member 212. The first frame member 212 and second frame member 214 are wedge shaped on the distal end, supporting a less invasive, lateral surgical approach. A locking collet 222, as illustrated in FIG. 11, is positioned on the first frame member 212, as illustrated in FIGS. 9 and 10. The locking collet 222 includes a set screw 224 positioned within a casing 226 disposed on the top of the locking collet 222. A rack 228 is formed within the inner bore of the locking collet 222 that corresponds with the height, width, and spacing of the rack 220 positioned on the first frame member 212. The rack 228 on the locking collet 222 is designed to form an integral relationship with the rack 220 positioned on the second frame member 214. The set screw 224 is designed to securely position the locking collet 222 onto the first frame member 212. The first frame member 212 and the second frame member 214, in conjunction with the locking collet 222, permit micromovement in flexion while preventing compression of the spine below a predefined length.

Each frame member 212, 214 includes a connector member 216, 218, as illustrated in FIGS. 9 and 10. The connector members 216, 218 are substantially arcuate in shape. The top portion of the connector members 216, 218 contains a bore 230 for receiving a bone screw 232 therethrough. Optionally, the top portion of the connector members 216, 218 contains a threaded bore 230 for receiving a correspondingly threaded bone screw 232 therethrough. The bottom portion of the connector members 216, 218 contains a sheath 234 for receiving the tip of the bone screw 232. The sheath 234 has a diameter slightly larger than the diameter of the head of the bone screw 232 for securely receiving the bone screw 232 within the sheath. The sheath 234 is designed to protect the tissues from the sharp tip of the bone screw 232. Optionally, the bore 230 may contain a seat (not illustrated) within the bore 230 for positioning the head of the bone screw 232. This exemplary embodiment also includes a pair of integral pads 236. An integral pad 236 is positioned on the first frame member 212, and an integral pad 236 is positioned on the second frame member 214. The pads 236 are designed for the attachment of a decompression/distraction instrument to the vertebral distraction device 210.

Figure 12:
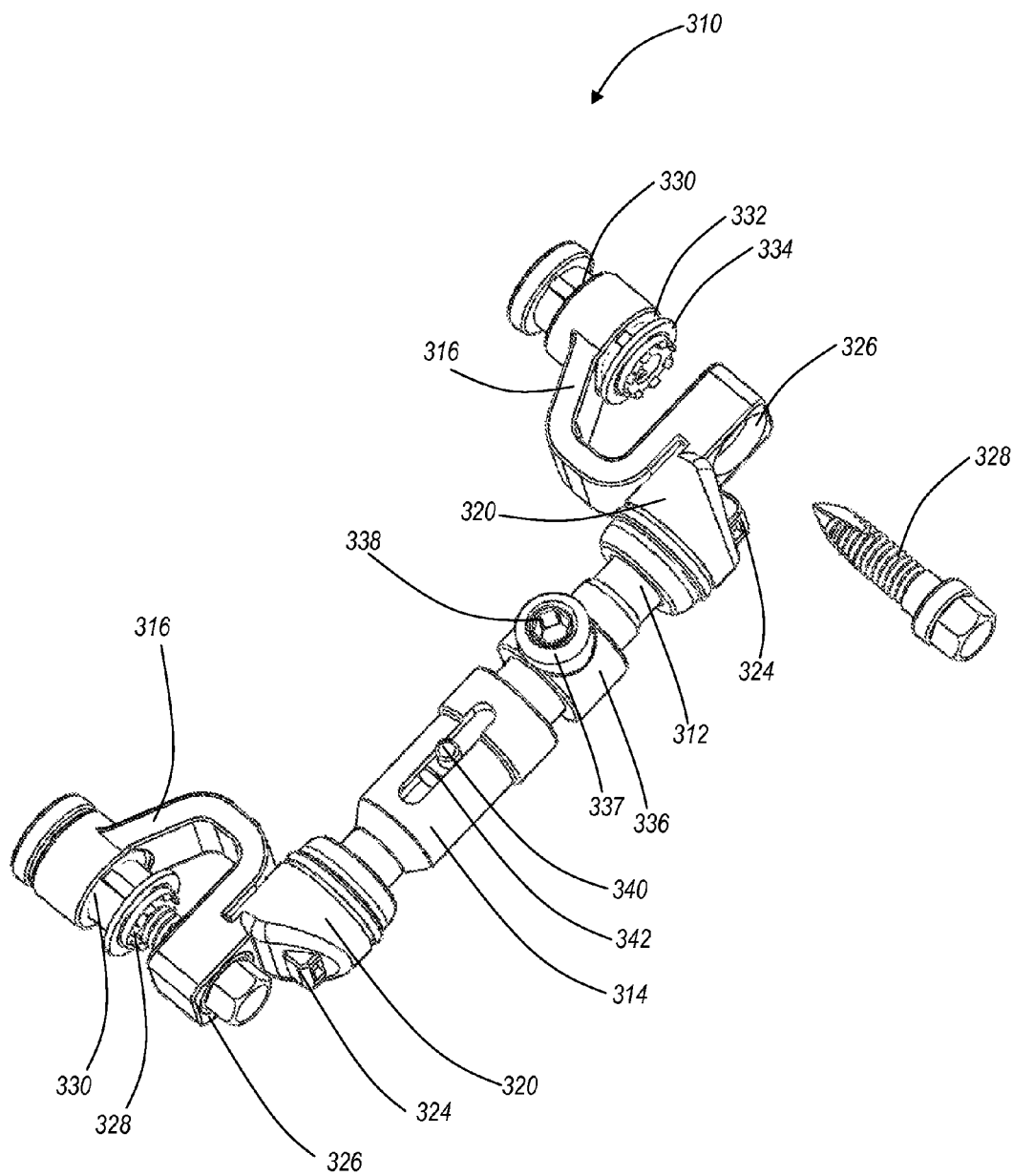
FIG. 12 is a perspective view of a still further exemplary embodiment of a vertebral stabilization device of the present invention.
Figure 13:
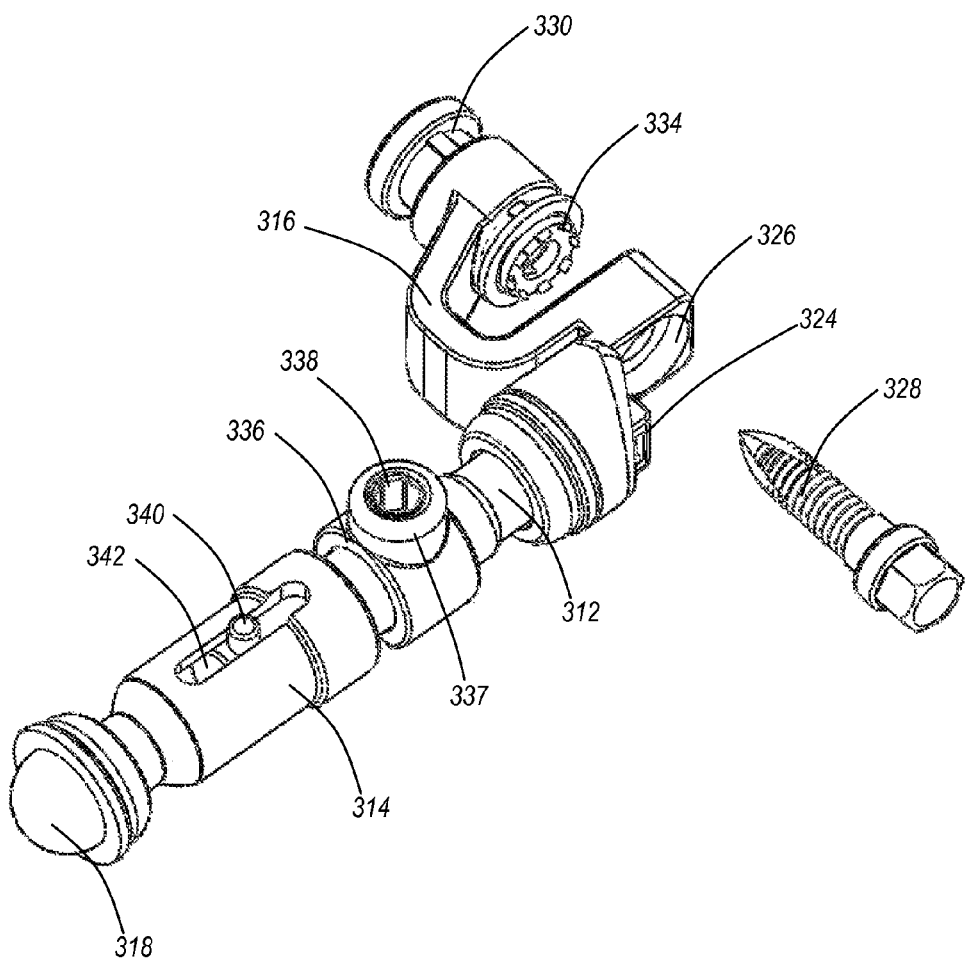
FIG. 13 is a partial perspective view of the vertebral stabilization device of FIG. 12.
Figure 14:
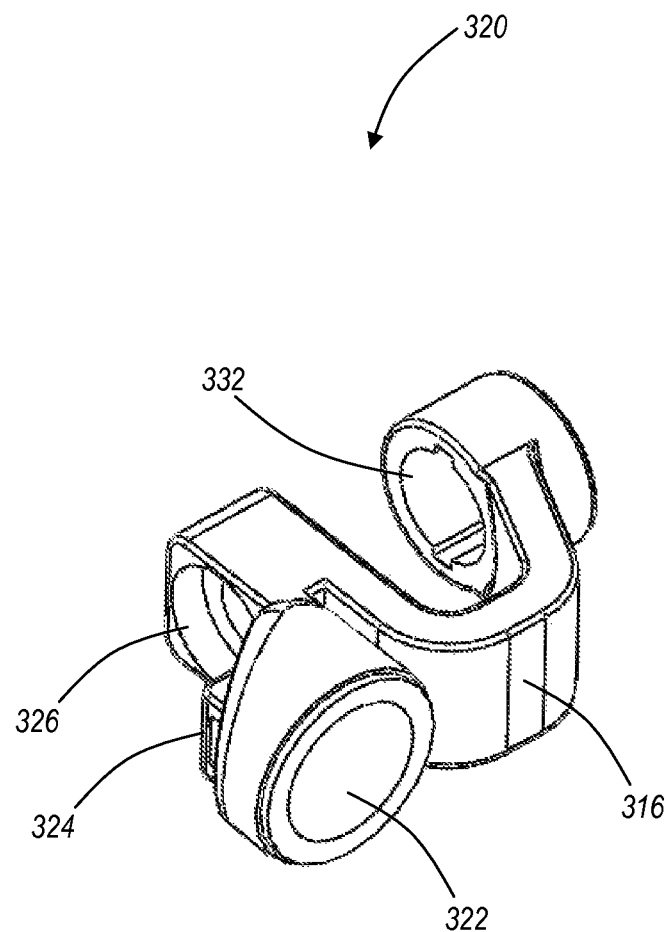
FIG. 14 is a perspective view of the connector member of the vertebral stabilization device of FIGS. 12 and 13.

Another exemplary embodiment of the vertebral stabilization device 310 is illustrated in FIG. 12. In this embodiment, the first frame member 312 and second frame member 314 each include a ball pivot 318, as illustrated in FIG. 13, located on a distal end of each frame member 312, 314. A ball joint housing 320 includes a recess 322, as illustrated in FIG. 14, located one the distal end of each frame member 312, 314. The ball pivot 318 of each frame member 312, 314 is pivotally mounted in the recess 322 of the ball joint housing 320. The ball joint housing 320 also includes an integral pad 324. The integral pad 324 is positioned on each ball joint housing 320 for the attachment of a decompression/distraction instrument to the vertebral stabilization device 310.

Each ball joint housing 320 includes a connector member 316, as illustrated in FIGS. 12 and 13. The top portion of the connector members 316 contains a bore 326 for receiving a bone screw 328 therethrough. Optionally, the top portion of the connector members 316 contains a threaded bore 326 for receiving a correspondingly threaded bone screw 328 therethrough. A distal washer 330 may be positioned within a bore 332 located on the bottom portion of the connector members 316. The distal washer 330 is designed to receive the tip of the bone screw 328, and slides laterally within the bore 326 for universal patient matching. Optionally, the bore 326 may contain a seat 334 within the bore 326 for positioning the head of the bone screw 328.

The first frame member 312 includes a rack with a plurality of ridges disposed on one side of the first frame member 312 (not illustrated). A locking collet 336 is also positioned on the first frame member 312. The locking collet 336 includes a set screw 338 positioned within a casing 337 disposed on the top of the locking collet 336. A rack is formed within the inner bore of the locking collet 336 that corresponds with the rack positioned on the second frame member 314 (not illustrated). The rack positioned on the locking collet 336 is designed to form an integral relationship with the rack positioned on the first frame member 312. The set screw 338 is designed to securely position the locking collet 336 onto the first frame member 312.

The first frame member 312 further includes a pin 340 positioned on an end of the frame member 312 opposite the ball joint housing 320. The pin 340 is received within a slot 342 positioned on the second frame member 314. The first frame member 312 and second frame member 314 are in a telescoping relationship with each other as defined by the length of the slot. The second frame member 314 is allowed to translate along the first frame member 312 at a distance as defined by the length of the slot 342. The movement of the second frame member 314 is prevented when the pin 340 contacts the ends of the slot 342.

The distal washer 330 provides for universal patient matching and increased stability and strength. The distal washer 330 allows the vertebral stabilization device 310 to be used on any patient with any thickness of spinous process, lamina, or sacrum. During insertion, as the screw 328 is advanced across the spinous process, for example, its threads engage and draw the distal washer 330 tight against the far cortical surface of the spinous process for stable and secure fixation to the spine. The screw length may vary such that the screw's distal end need not project past the washer when fully engaged to the spinous process, thus preventing tissue damage that may be caused by a sharp, self-tapping screw point. The first frame member 312, second member 314, locking collet 336, ball pivot 318, and ball joint housing 320 work in conjunction to permit both decompression and dynamic fixation of the spine.

Figure 15:
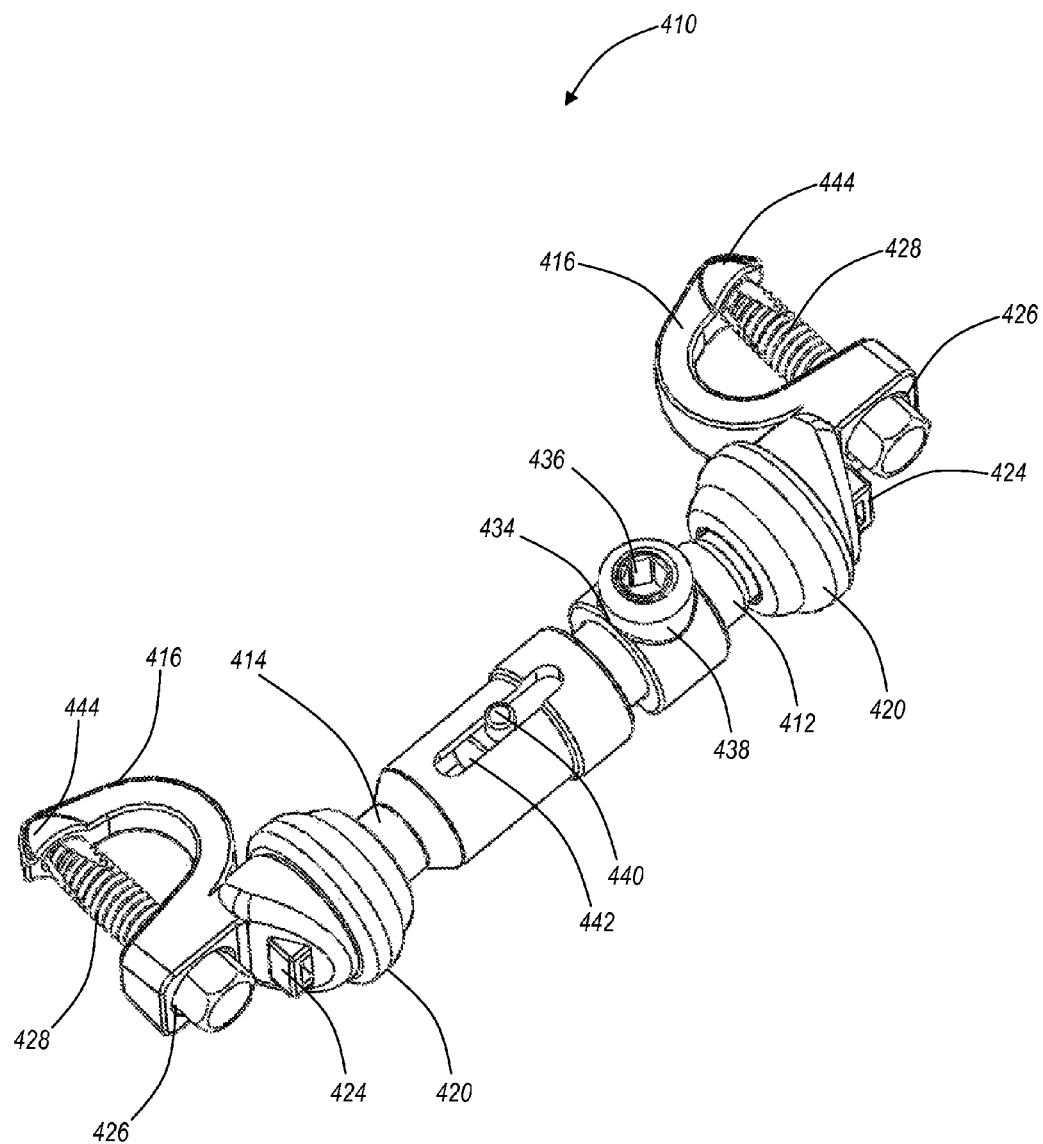
FIG. 15 is a perspective view of a still further exemplary embodiment of a vertebral stabilization device of the present invention.

Another exemplary embodiment of the vertebral stabilization device 410 is illustrated in FIG. 15. In this embodiment, the first frame member 412 and second frame member 414 each include a ball pivot (not illustrated) located on a distal end. A ball joint housing 420 that includes a recess (not illustrated) is also located at the distal end of each frame member 412, 414. The ball pivot of each frame member 412, 414 is pivotally mounted in a recess of the ball joint housing 420. The ball joint housing 420 also includes an integral pad 424. The integral pad 424 is positioned on each ball joint housing 420 for attachment of a decompression/distraction instrument.

Figure 16:
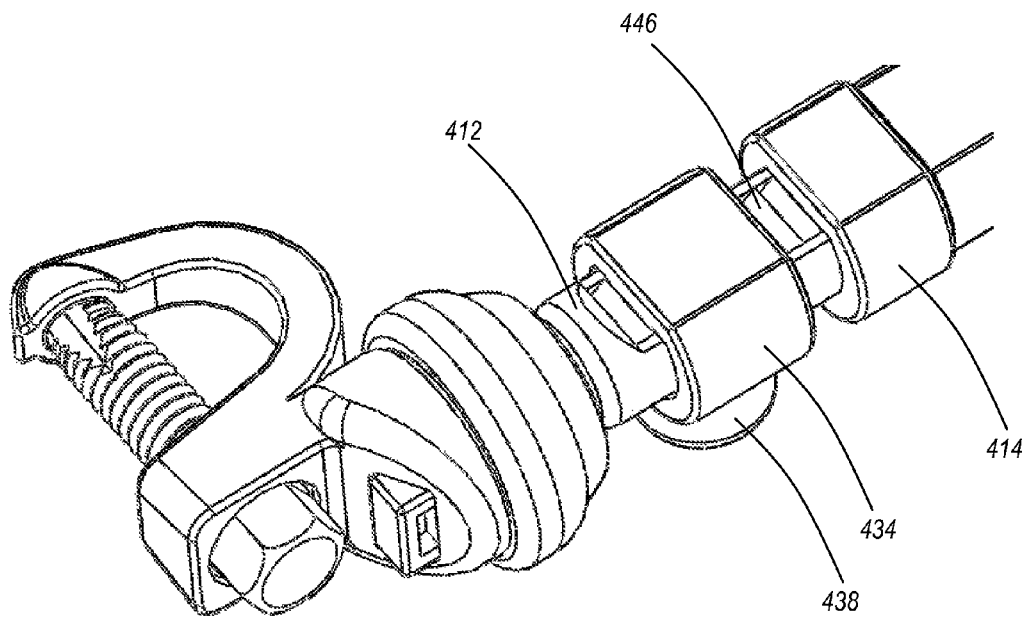
FIG. 16 is a partial perspective view of the vertebral stabilization device of FIG. 15.

Each ball joint housing 420 includes a connector member 416, as illustrated in FIGS. 15 and 16. The connector members 416 are substantially arcuate in shape. The top portion of the connector members 416 contains a bore 426 for receiving a bone screw 428 therethrough. Optionally, the top portion of the connector members 416 contains a threaded bore 426 for receiving a correspondingly threaded bone screw 428 therethrough. A sheath 444 is located on the bottom portion of the connector members 416 for receiving the tip of the bone screw 428. The sheath 444 has a diameter that is slightly larger than the diameter of the tip of the bone screw 428 for securely receiving the bone screw 428 within the sheath 444. The sheath 444 is designed to protect tissues from the sharp tip of the bone screw 428. Optionally, the bore 426 may contain a seat (not illustrated) within the bore 426 for positioning the head of the bone screw 428.

Figure 17:
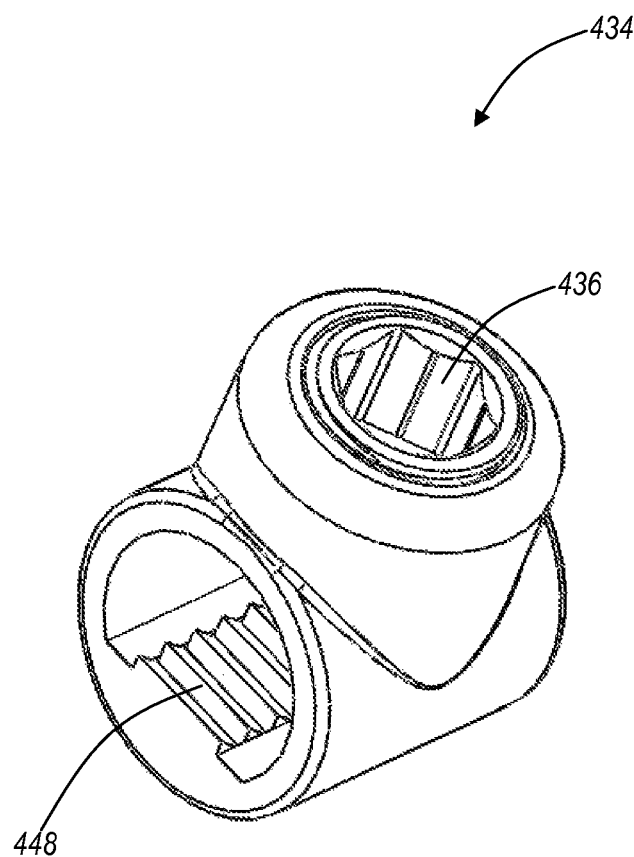
FIG. 17 is a perspective view of the locking collet of the vertebral stabilization device of FIGS. 15 and 16.

The first frame member 412 includes a rack 446 with a plurality of ridges disposed on one side of the first frame member 412, as illustrated in FIG. 16. A locking collet 434 is positioned on the first frame member 412. The locking collet 434 includes a set screw 436 positioned within a casing 438 disposed on the top of the locking collet 434. A rack 448 is formed within the inner bore of the locking collet 434 that corresponds with the rack 446 positioned on the first frame member 412, as illustrated in FIG. 17. The rack 448 on the locking collet 434 is designed to form an integral relationship with the rack 446 positioned on the first frame member 412. The set screw 436 is designed to securely position the locking collet 434 onto the first frame member 412.

The first frame member 412 further includes a pin 440 positioned on an end opposite the ball joint housing 420. The pin 440 is received within a slot 442 positioned on the second frame member 414. The first frame member 412 and second frame member 414 are in a telescoping relationship with each other as defined by the length of the slot 442. In other words, the second frame member 414 is allowed to translate along the first frame member 412 at a distance as defined by the length of the slot 442. The movement of the second frame member 414 is prevented when the pin 440 contacts the ends of the slot 442, thus ceasing further telescoping movement.

The first frame member 412, second frame member 414, locking collet 434, ball pivot 418, and ball joint housing 420 work in conjunction to permit both decompression and dynamic stabilization of the spine. The first frame member 412 and second frame member 414 have a wedge shaped design at the distal end to support a less invasive, lateral surgical approach.

Figure 18:
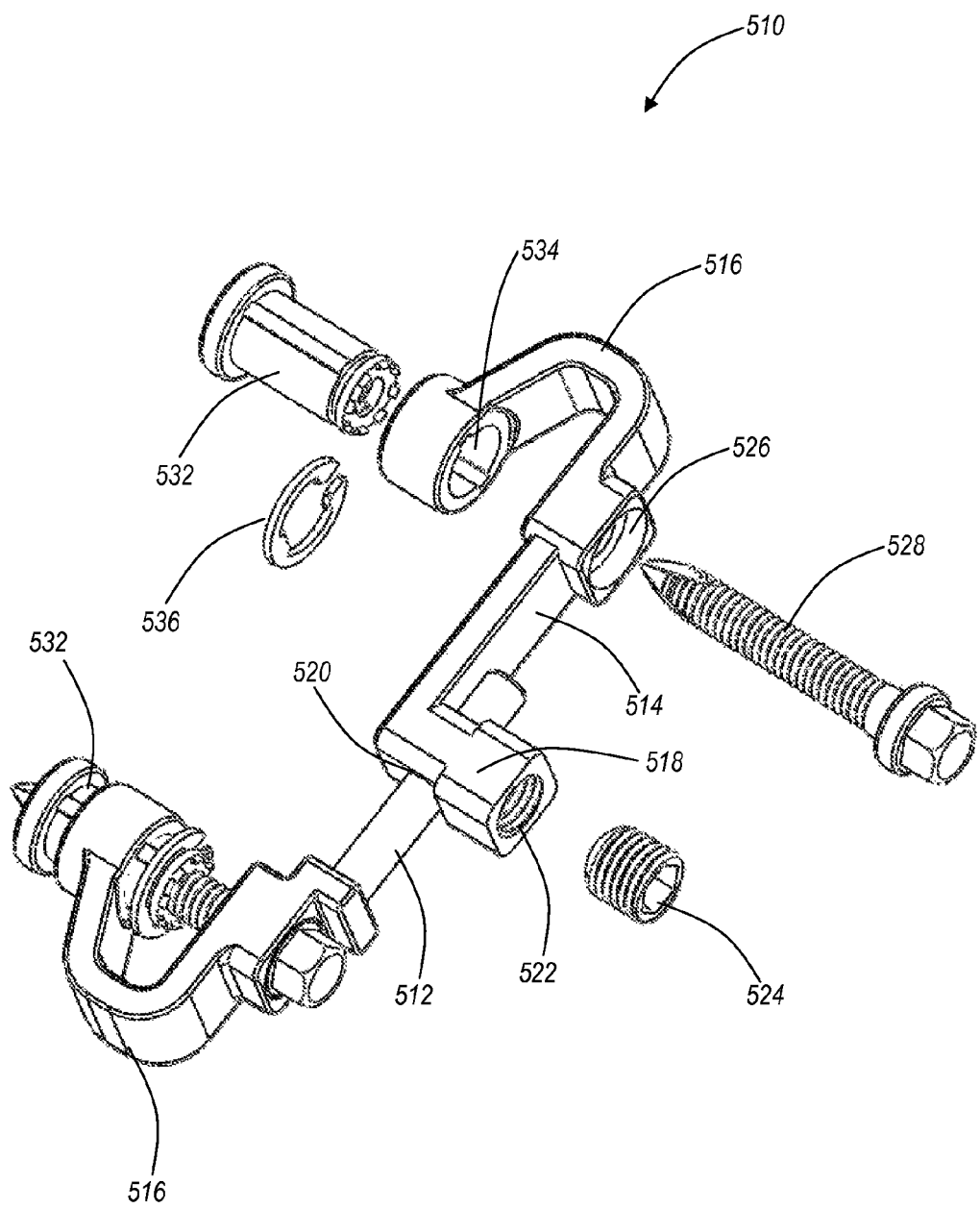
FIG. 18 is a perspective view of a still further exemplary embodiment of a vertebral stabilization device of the present invention.

FIG. 18 illustrates another exemplary embodiment of the vertebral stabilization device 510. As illustrated, the vertebral stabilization device 510 has a first frame member 512 and a second frame member 514. The first frame member 512 and second frame member 514 are in a telescopic relationship with each other. Specifically, the first frame member 512 is partially received within the second frame member 514 for attaching the first frame member 512 to the second frame member 514 and allowing the first frame member 512 and second frame member 514 to collectively expand and contract.

The second frame member 514 contains an upright 518 on the distal end. The upright 518 contains a horizontal bore 520 and a vertical bore 522. The horizontal bore 520 is designed to receive the first frame member 512. The vertical bore 522 is threaded to receive a correspondingly threaded set screw 524. The set screw 524 contains a recess for receiving a tool to rotate the set screw 524 within the vertical bore 522. As the set screw 524 is rotated, the base of the set screw 524 secures the first frame member 512 within the horizontal bore 520.

Each frame member 512, 514 includes a connector member 516, as illustrated in FIG. 18. The connector members 516 are substantially arcuate in shape. The top portion of the connector members 516 contains a bore 526 for receiving a bone screw 528 therethrough. Optionally, the top portion of the connector member 516 contains a bore 526 for receiving a correspondingly threaded bone screw 528 therethrough. Optionally, the bore 526 may contain a seat (not illustrated) within the bore 526 for positioning the head of the bone screw 528. A distal washer 532 may be positioned within a bore 534 located on the bottom portion of the connector member 516. The distal washer 532 is designed to receive the tip of the bone screw 528, and slides laterally within the bore 534 for universal patient matching. The distal washer 532 is retained with the bore 526 by a snap ring 536 that allows the distal washer 532 to slide laterally, but not separate from the connector member 516.

The distal washer 532 provides for universal patient matching and increased stability and strength. The distal washer 532 allows the vertebral stabilization device 510 to be used on any patient with any thickness of spinous process, lamina, or sacrum. During insertion, as the screw 528 is advanced across the spinous process, its threads engage and draw the distal washer 532 tight against the far cortical surface of the spinous process for stable and secure fixation to the spine. The screw length may vary such that the screw's distal end need not project past the washer when fully engaged to the spinous process, thus preventing tissue damage that may be caused by a sharp, self-tapping screw point.

Figure 19:
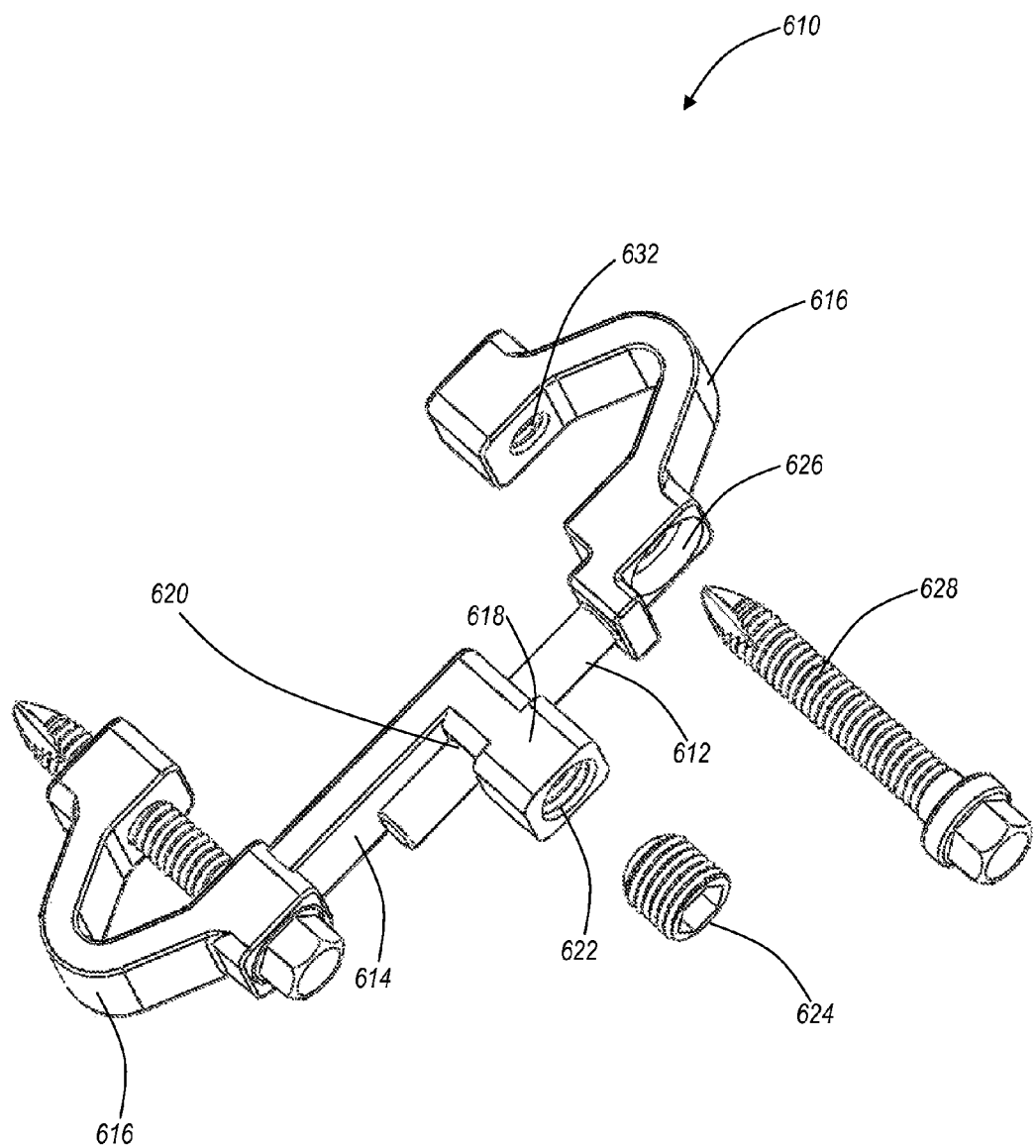
FIG. 19 is a perspective view of a still further exemplary embodiment of a vertebral stabilization device of the present invention.

FIG. 19 illustrates another exemplary embodiment of the vertebral stabilization device 610. As illustrated, the vertebral stabilization device 610 has a first frame member 612 and a second frame member 614. The first frame member 612 and second frame member 614 are in a telescopic relationship with each other. Specifically, the first frame member 612 is partially received within the second frame member 614 for attaching the first frame member 612 to the second frame member 614 and allowing the first frame member 612 and second frame member 614 to collectively expand and contract.

The second frame member 614 contains an upright 618 on the distal end. The upright 618 contains a horizontal bore 620 and a vertical bore 622. The horizontal bore 620 is designed to receive the first frame member 612. The vertical bore 622 is threaded to receive a correspondingly threaded set screw 624. The set screw 624 contains a recess for receiving a tool to rotate the set screw 624 within the vertical bore 622. As the set screw 624 is rotated, the base of the set screw 624 secures the first frame member 612 within the horizontal bore 620. The set screw 624 locks the first frame member 612 during post distraction or compression.

Each frame member 612, 614 includes an connector member 616, as illustrated in FIG. 19. The connector members 616 are substantially arcuate in shape. The top portion of the connector members 616 contains a bore 626 for receiving a bone screw 628. Optionally, the top portion of the connector members 616 contains a bore 626 for receiving a correspondingly threaded bone screw 628 therethrough. Optionally, the bore 626 may contain a seat (not illustrated) within the bore 626 for positioning the head of the bone screw 628. The bottom portion of the connector members 616 contains a threaded bore 632 for receiving the correspondingly threaded bone screw 628. Alternatively, the connector members 616 may be rotated 180 degrees for distraction of the spine.

The bores 626, 632 positioned within the connector member 616 aid in the predictable placement of the bone screw 628 by acting as a guide. During insertion, as the bone screw 628 is advanced across the spinous process, lamina, or sacrum, its threads engage and draw the distal end of the connector members 616 for stable and secure fixation to the spine. The screw length may vary such that the screw's distal end need not project past the connector member 616 when fully engaged to the spinous processes, lamina, or sacrum, thus preventing tissue damage that may be caused by a sharp, self-tapping screw point.

The vertebral stabilization devices of the present invention may be formed of a variety of materials. For example, where a given vertebral stabilization device has a surface that contacts another surface, the surfaces may be formed from biocompatible metals, such as cobalt chromium, chromium steel, surgical steel, titanium, titanium alloys, tantalum, tantalum alloys, aluminum, or the like. Suitable ceramics or other suitable biocompatible materials known in the art may also be utilized. Suitable polymers include polyesters, aromatic esters, such as polyalkylene terephthalates, polyamides, polyalkenes, poly(vinyl)fluoride, PTFE, polyarylethyl ketone, and the like.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A vertebral stabilization device operable for stabilizing and/or decompressing a portion of the spine, comprising:
    a first frame member comprising a first plurality of bone screw openings, wherein the first plurality of bone screw openings extend all the way through the first frame member such that a bone screw can extend through one of the first plurality of bone screw openings and into a bone of the spine, and wherein the first plurality of bone screw openings extend in at least a substantially linear fashion;
    a second frame member comprising a second plurality of bone screw openings, wherein the second plurality of bone screw openings extend all the way through the second frame member such that a bone screw can extend through one of the second plurality of bone screw openings and into a bone of the spine, and wherein the second plurality of bone screw openings extend in at least a substantially linear fashion;
    a first connector member engaged to the first frame member for securing the first frame member to a first structure of the spine;
    a second connector member engaged to the second frame member for securing the second frame member to a second structure of the spine;
    a first bone screw configured to be selectively disposed through at least one of the first plurality of bone screw openings of the first frame member and configured to extend into the first structure of the spine adjacent to the first connector member; and
    a second bone screw configured to be selectively disposed through at least one of the second plurality of bone screw openings of the second frame member and configured to extend into the second structure of the spine adjacent to the second connector member;
    wherein the first frame member and the second frame member are in a telescoping relationship with each other such that the first frame member is configured to be at least partially received within the second frame member for forming the telescoping relationship, wherein movement of the first frame member within the second frame member is supported by at least substantially an entire length of the second frame member receiving the first frame member, apd wherein telescoping portions of the first frame member and second frame member are configured such that rotation with respect to each other is inhibited, wherein the first frame member comprises a longitudinal axis, wherein the second frame member comprises a longitudinal axis, wherein the first frame member is configured to be at least partially received within the second frame member at least substantially along the longitudinal axes of the first and second frame members, wherein the first plurality of bone screw openings extend in a direction at least substantially perpendicular to the longitudinal axis of the first frame member, and wherein the second plurality of bone screw openings extend in a direction at least substantially perpendicular to the longitudinal axis of the second frame member.

2. The vertebral stabilization device according to claim 1, wherein the first connector member and the second connector member are substantially arcuate in shape.

3. The vertebral stabilization device according to claim 1, further comprising a securement mechanism positioned on the second frame member for providing a secured arrangement between the first frame member and the second frame member.

4. The vertebral stabilization device according to claim 1, wherein at least a subset of the first plurality of bone screw openings comprises mutually overlapping receiving bores.

5. A vertebral stabilization device operable for stabilizing and/or decompressing a portion of the spine comprising:
    a first frame member comprising a first plurality of bone screw openings, wherein the first plurality of bone screw openings extend all the way through the first frame member such that a bone screw can extend through one of the first plurality of bone screw openings and into a bone of the spine, wherein the first frame member comprises a longitudinal axis, and wherein the first plurality of bone screw openings extend in a direction at least substantially perpendicular to the longitudinal axis of the first frame member;
    a second frame member comprising a second plurality of bone screw openings, wherein the second plurality of bone screw openings extend all the way through the second frame member such that a bone screw can extend through one of the second plurality of bone screw openings and into a bone of the spine, and wherein the second frame member further comprises a non-circular recess defined by the body of the second frame member for at least partially receiving a portion of the first frame member having a non-circular cross-section, forming a telescoping relationship between the first frame member and the second frame member, wherein the telescoping relationship is configured such that the first frame member is at least substantially prevented from pivoting relative to the second frame member while the first frame member is at least partially received in the second frame member, wherein the second frame member comprises a longitudinal axis and wherein the second plurality of bone screw openings extend in a direction at least substantially perpendicular to the longitudinal axis of the second frame member wherein the first frame member is configured to be at least partially received within the second frame member at least substantially along the longitudinal axes of the first and second frame members;

a first connector member engaged to the first frame member for securing the first frame member to a first structure of the spine;

a second connector member engaged to the second frame member for securing the second frame member to a second structure of the spine;

a securement mechanism for securing the first frame member to the second frame member and preventing telescoping movement of the first frame member with respect to the second frame member;

a first bone screw configured to be selectively disposed through at least one of the first plurality of bone screw openings of the first frame member and configured to extend into the first structure of the spine adjacent to the first connector member; and a second bone screw configured to be selectively disposed through at least one of the second plurality of bone screw openings of the second frame member and configured to extend into the second structure of the spine adjacent to the second connector member.

6. The vertebral stabilization device according to claim 5, wherein the securement mechanism comprises a set screw positioned on the second frame member for preventing telescoping movement between the first frame member and the second frame member.

7. The vertebral stabilization device according to claim 1, wherein the telescoping portions of the first frame member and the second frame member have substantially rectangular cross-sections.

8. The vertebral stabilization device according to claim 1, wherein the first frame member comprises a ridge configured to restrict the telescoping movement of the first frame member relative to the second frame member.

9. The vertebral stabilization device according to claim 5, wherein the first frame member comprises a ridge configured to restrict the telescoping movement of the first frame member relative to the second frame member.

10. The vertebral stabilization device according to claim 1, wherein at least a subset of the second plurality of bone screw openings comprises mutually overlapping receiving bores.

11. The vertebral stabilization device according to claim 4, wherein at least a subset of the second plurality of bone screw openings comprises mutually overlapping receiving bores.

12. The vertebral stabilization device according to claim 1, wherein the first frame member further comprises a widened portion configured to accommodate the first plurality of bone screw openings, and wherein the second frame member further comprises a widened portion configured to accommodate the second plurality of bone screw openings.

* * * * *